United States Patent
Ware et al.

(10) Patent No.: US 9,011,838 B2
(45) Date of Patent: Apr. 21, 2015

(54) LOW/HIGH DOSE PROBIOTIC SUPPLEMENTS AND METHODS OF THEIR USE

(75) Inventors: Douglas Ware, Chapel Hill, NC (US); Peter Anderson, Leawood, KS (US)

(73) Assignee: Nutrition Physiology Company, LLC, Guymon, OK (US)

(*) Notice: Subject to any disclaimer, the term of this patent is extended or adjusted under 35 U.S.C. 154(b) by 852 days.

(21) Appl. No.: 12/763,775

(22) Filed: Apr. 20, 2010

(65) Prior Publication Data

US 2011/0256116 A1 Oct. 20, 2011

(51) Int. Cl.
| | |
|---|---|
| A61K 35/74 | (2006.01) |
| A61P 31/00 | (2006.01) |
| C12N 1/20 | (2006.01) |
| A61K 38/47 | (2006.01) |
| C12N 1/04 | (2006.01) |
| C12P 1/04 | (2006.01) |

(52) U.S. Cl.
CPC .............. *A61K 35/74* (2013.01); *A61K 38/47* (2013.01); *A61K 2300/00* (2013.01)

(58) Field of Classification Search
USPC ............... 424/93.45; 435/41, 243, 252.9
See application file for complete search history.

(56) References Cited

U.S. PATENT DOCUMENTS

| | | | | |
|---|---|---|---|---|
| 5,179,020 | A * | 1/1993 | Herman et al. | 435/252.9 |
| 6,455,063 | B1 * | 9/2002 | Rehberger et al. | 424/438 |
| 7,063,836 | B2 * | 6/2006 | Garner et al. | 424/93.45 |
| 7,291,327 | B2 * | 11/2007 | Garner et al. | 424/93.45 |
| 7,888,062 | B1 * | 2/2011 | Garner et al. | 435/41 |
| 8,734,785 | B2 * | 5/2014 | Garner et al. | 424/93.45 |
| 2008/0057045 | A1 | 3/2008 | Garner et al. | |

OTHER PUBLICATIONS

Galyean et al. (2000. Effect of Live Cultures of *Lactobacillus acidophilus* (strains 45 and 51) and *Propionibacterium freudenreichii* PF-24 on performance and carcass characteristics of finishing beef steers. Burnett Center Internet Progress Report, No. 8, Nov. 2000, pp. 1-12).*

N.A. Elam, et al., "Effects of Live Cultures of *Lactobacillus acidophilus* (strains NP45 and NP51) and *Propionibacterium freudenreichii* on Performance, Carcass, and Intestinal Characteristics, and *Escherichia coli* Strain O157 Shedding of Finishing Beef Steers." Journal of Animal Science, 2003, vol. 81, No. 11, pp. 2686-2698.

C.R Krehbiel, et al. "Bacterial Direct-Fed Microbials in Ruminant diets: Performance Response and Mode of Action" Journal of Animal Science, 2003, vol. 81, No. 14 (Suppl 2), pp. E120-E132.

J.T. Vasconcelos, et al. Effects of Increasing Dose of Live Cultures of *Lactobacillus acidophilus* (Strain NP 51) Combined With Single Dose of *Propionibacterium freudenreichii* (Strain NP 24) on performance and Carcass, Journal of Animal Science, vol. 86, No. 3, pp. 756-762 (2007).

International Search Report and Written Opinion issued in related PCT Patent Application Serial No. PCT/US2011/033267, dated Dec. 26, 2011, 10 pages.

* cited by examiner

*Primary Examiner* — Jon P Weber
*Assistant Examiner* — Kailash C Srivastava
(74) *Attorney, Agent, or Firm* — Lathrop & Gage LLP

(57) ABSTRACT

Methods and compositions are hereby disclosed for reducing the numbers of *E. coli* O157:H7, *Salmonella* or other pathogens in an animal. The methods include administering to the animal a lactic acid producing bacterium at a relatively low dosage in combination with a lactate utilizing bacterium, followed by administration of the lactic acid producing bacterium at a relatively high dosage. The disclosed methods help achieve pre-harvest food safety and enhance feed performance while keeping the total cost relatively low. The preferred lactic acid producing bacterium is *Lactobacillus acidophilus/animalis* and the preferred lactate utilizing bacterium is *Propionibacterium freudenreichii*.

16 Claims, 3 Drawing Sheets

LOW/HIGH DOSE PROBIOTIC SUPPLEMENTS AND METHODS OF THEIR USE

BACKGROUND

1. Field of the Invention

The present disclosure pertains to the use of lactic acid bacteria as a feed supplement to enhance the feed performance and to reduce pathogenic infection in an animal, such as a ruminant. More particularly, the disclosure relates to a unique combination of low dose and high dose bacteria supplement to enhance feed performance and to reduce pathogenic infections in the animal.

2. Description of Related Art

Pathogens have been known to cause illnesses in animals, including humans. Pathogens may cause a wide variety of illnesses ranging from mild disorders to fatal diseases. Examples of such illnesses include weight loss, diarrhea, abdominal cramping, and renal failure, among others.

Extreme health risks may result when humans consume food products that have been contaminated with pathogens. Food products that are most vulnerable to such contamination include sprouts, lettuce, meat products, unpasteurized milk and juice, and water, among others. The problem is particularly prevalent in the beef and dairy industry. Pathogens present on a cow's udder or on milking equipment may find their way into raw milk. Meat can become contaminated at the slaughter house, and pathogenic organisms can be mixed into large quantities of meat when it is ground. This problem is difficult to solve because contaminated meat often looks and smells perfectly normal. Furthermore, the number of pathogenic organisms needed to cause disease is extremely small, and detection of such small number of pathogens is extraordinarily difficult.

Pathogens that cause diseases in the intestinal tract are commonly known as enteropathogens. Examples of enteropathogenic bacteria include *Staphylococcus aureus*, certain strains of *Escherichia coli* (*E. coli*), and *Salmonella* spp. While most of the hundreds of strains of *E. coli* are harmless and live in the intestines of animals, including humans, some strains, such as *E. coli* O157:H7, O111:H8, and O104:H21, produce large quantities of powerful shiga-like toxins that are closely related to or identical to the toxin produced by *Shigella dysenteriae*. These toxins can cause severe distress in the small intestine, often resulting in damage to the intestinal lining and resulting in extreme cases of diarrhea. *E. coli* O157:H7 can also cause acute hemorrhagic colitis, characterized by severe abdominal cramping and abdominal bleeding. In children, this can progress into the rare but fatal disorder called hemolytic uremic syndrome ("HUS"), characterized by renal failure and hemolytic anemia. In adults, it can progress into an ailment termed thrombotic thrombocytopenic purpura ("TTP"), which includes HUS plus fever and neurological symptoms and can have a mortality rate as high as fifty percent in the elderly.

Food borne pathogen contamination may be controlled by minimizing contamination at several points of entry by pathogens. Pre-harvest control of pathogens by the beef industry such as by reducing pathogen shedding in feces, has been recognized as an important point of control. Beyond this point, pathogens can find many different ways into the food chains, for example, through potential runoff contamination, contact with humans, or cross contamination during meat processing.

U.S. Pat. No. 7,063,836 disclosed a unique combination of lactic acid producing bacterium and lactate utilizing bacterium as feed supplements (also known as direct-fed microbials (DFM) or probiotics) to help reduce pre-harvest infections in ruminants. The compositions and methods disclosed in U.S. Pat. No. 7,063,836 help reduce the numbers of enteropathogens such as *E. coli* O157:H7. By reducing the numbers of enteropathogens in animals that produce meat or milk, these methods help protect consumers of beef, dairy, and other food products from being infected by the pathogens.

A number of studies have been conducted to determine the effects of different dosages of the DFM on feed performance and pathogen reduction. Stephens et al. compared the recovery of *E. coli* O157 or *Salmonella* in cattle fed with the low ($10^7$), medium ($10^8$) and high ($10^9$) dose of *Lactobacillus acidophilus/animalis* NP51 (also known as LA51, or NPC747), in conjunction with $1\times10^9$ CFU of *Propionibacterium freudenreichii* NP24 (also known as PF24). *Journal of Food Protection*, Vol. 70, No. 10, Pages 2386-2391 (2007). Above the dosage of $10^7$ CFU per animal per day, no significant dose-response of NP51 on recovery of *E. coli* O157 or *Salmonella* was detected when used in conjunction with a fixed dosage of PF24. Thus, according to Stephens et al., the low and high doses were about equally effective in reducing the recovery of *E. coli* O157. Id. at p2390. For reduction of *Salmonella*, the high dose of NP51 supplementation appeared to be the most effective among the three doses in reducing *Salmonella* in feces or on hides of feedlot cattle. Id. In a separate study, Vasconcelos et al. reported that the dosage of NP51 has no significant effects on average daily weight gain when used in conjunction with a fixed dosage of PF24. *J. Animal Science*, 86:756-762 (2008). In fact, feed performance, as measured by carcass-adjusted gain to feed ratio (G:F) and dressing percentage, decreased with increasing dosage of the NP51 when used in conjunction with a fixed dosage of PF24. Id. These studies all point to a conclusion that the ideal DFM program for improving biological performance of feedlot cattle would have a different dosage of DFM than the ideal program for reducing the numbers of pathogenic bacteria. Thus, at the time of the present invention, it appeared impossible to have a single program that meets both goals of achieving high feed performance while reducing pathogenic bacteria.

SUMMARY OF INVENTION

The present disclosure advances the art by providing methods and compositions for reducing pathogenic infection in animals and enhancing feed performance. The compositions preferably include a lactic acid producing bacterium and a lactate utilizing bacterium. In one embodiment, the animals' diet may be supplemented with at least one lactic acid producing bacterium at a dosage of between $1\times10^5$ and $5\times10^7$ CFU per day, or more preferably, about $10^7$ CFU per day per animal, in combination with at least one lactate utilizing bacterium at a dosage of between $5\times10^8$ and $5\times10^9$ CFU per day, or more preferably, about $10^9$ CFU per day per animal. Approximately 20-60 days prior to harvest (or sacrifice), the dosage of the lactic acid producing bacteria may be increased to between $5\times10^8$ and $5\times10^9$ CFU per day, or more preferably, about $10^9$ CFU per day per animal, while maintaining the same dosage of the lactate utilizing bacteria at about $10^9$ CFU, per day per animal. The present methods help reduce pathogenic infection and increase feed performance with only a modest increase of cost attributable to the cost of the DFM.

In another embodiment, the animals' diet may be supplemented with at least one lactic acid producing bacterium at a dosage of between $1\times10^5$ and $5\times10^7$ CFU, or more preferably, about $10^7$ CFU per day per animal. Approximately 20-60 days prior to harvest (or sacrifice), the dosage of the lactic acid producing bacteria may be increased to between $5 \times 10^8$ and $5 \times 10^9$ CFU per day, or more preferably, about $10^9$ CFU per day per animal.

The disclosed methods may be applicable in many animal types, for example, cows, sheep, pigs, goats, birds, among others. In one preferred embodiment, the animals of the present disclosure are ruminants. Prior reports have suggested that feed performance may not improve when animals are fed a high dose of the lactic acid producing bacterium. However, under the feeding scheme disclosed herein, excellent feed performance and pathogen reduction may both be achieved when the animals are first fed with a low dosage of a lactic acid producing bacterium in conjunction with a fixed dose of a lactate utilizing bacterium from the beginning of the feeding period before being switched to a diet containing high dosage of the same lactic acid producing bacterium and the same fixed dose of the same lactate utilizing bacterium for at least 20 days.

In one aspect, the low dose feeding involves feeding the animal a lactic acid producing bacterium between $1 \times 10^5$ and $5 \times 10^7$ CFU per day either alone or in combination with a lactate utilizing bacterium between $5 \times 10^8$ and $5 \times 10^9$ CFU per day for at least 30 days. More preferably, the low dose feeding involves feeding the animal a lactic acid producing bacterium between $8 \times 10^6$ and $2 \times 10^7$ CFU per day, or even more preferably, about $10^7$ CFU per day, either alone or in combination with a lactate utilizing bacterium between $8 \times 10^8$ and $2 \times 10^9$ CFU per day for at least 30 days.

In another aspect, the high dose feeding involves feeding the animal a lactic acid producing bacterium between $5 \times 10^8$ and $5 \times 10^9$ CFU per day either alone or in combination with a lactate utilizing bacterium between $5 \times 10^8$ and $5 \times 10^9$ CFU per day for 20-60 days. More preferably, the high dose feeding involves feeding the animal a lactic acid producing bacterium between $8 \times 10^8$ and $2 \times 10^9$ CFU per day, or even more preferably, about $10^9$ CFU per day, either alone or in combination with a lactate utilizing bacterium between $8 \times 10^8$ and $2 \times 10^9$ CFU per day for 20-60 days.

The low dose feeding may be started on calves. Preferably, the low dosage of a lactic acid producing bacterium may be started when the cattle are placed on feed about 120-360 days prior to harvesting, and may continue until the animals are switched to feeds containing high dosage of a lactic acid producing bacterium for at least 20 days, preferably for 20-60 days, or more preferably, for about 30 days at the end of the feeding period. After the high dose feeding ends, the animals are slaughtered on site or are sent off to be slaughtered off site. The high dose supplementation of a lactic acid producing bacterium may be continued until the animal is sacrificed. It is to be understood that there may be a time gap between the low dose and high dose feeding periods. Such a gap between the end of the low dose feeding period and the start of the high dose period may last 0-10 days, but a gap of 0 day is preferable. There may also be a time gap between the time when the animal is taken off the high dose supplementation of lactic acid producing bacterium and the time when the animal is sacrificed. The gap between the end of the high dose feeding period and sacrifice may last 0-10 days, but a gap of 0 day is preferable.

For the purpose of this disclosure, it is preferred that the animals be fed daily with either the low dose or high dose lactic acid producing bacteria either alone or in combination with the lactate utilizing bacteria during the low dose or high dose periods, respectively. However, it is conceivable that sometimes certain days may pass by and the animals may not have been fed with the low dose or high dose lactic acid producing bacteria. Feeding of the animals according to the low dose/high dose methods disclosed herein on a discontinuous basis may still help achieve some or all of the beneficial effects described herein, and therefore such discontinuous feeding is still within the scope of the present disclosure.

The disclosed methods may be applicable for reducing infection caused by a number of different pathogens, such as, by way of example, bacterium, virus, fungus. More preferably, the pathogen is a bacterium selected from the group consisting of *Escherichia coli*, *Salmonella* spp., and *Staphylococcus aureus*, and even more preferably, the pathogen is *Escherichia coli* O157:H7.

DETAILED DESCRIPTION

Figure 1:
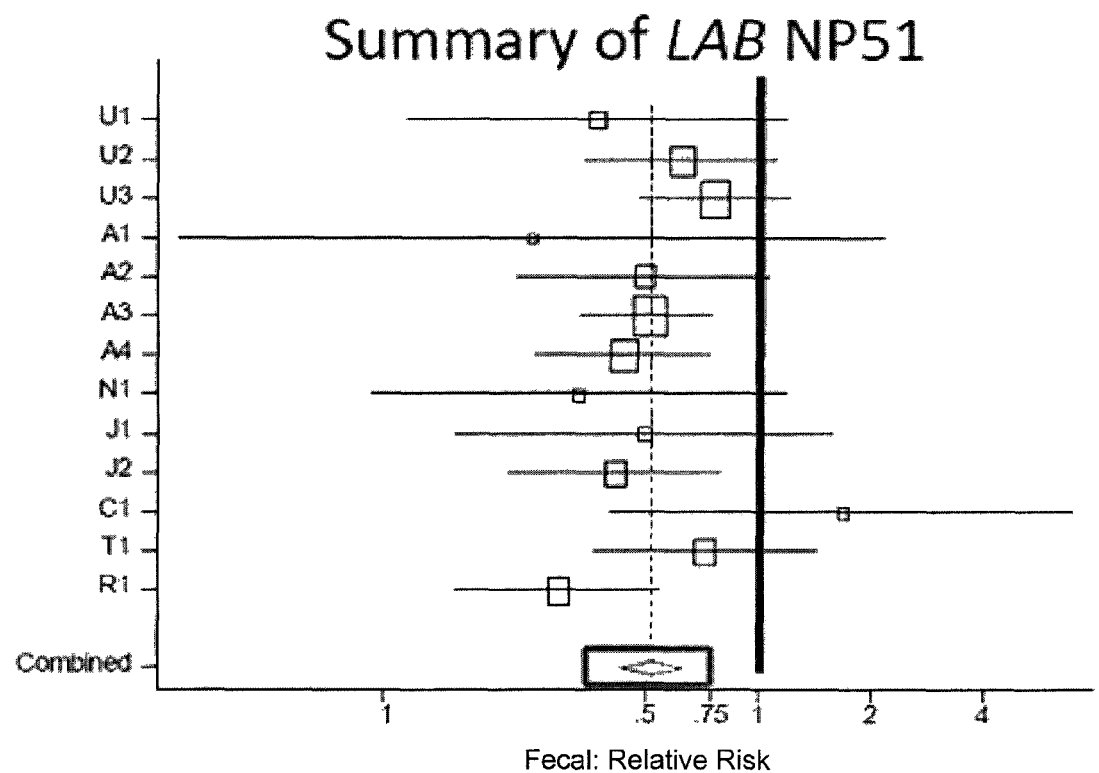
FIG. 1 shows the results of the Meta-analysis showing reduction of O157:H7 prevalence in feces by Bovamine® Culture Complex (CC) over control.

This disclosure provides improved methods for enhancing the feed efficiency while reducing pathogenic bacteria in animals without drastically increasing the feeding cost.

In one embodiment, Bovamine® Rumen Culture (RC) is used to enhance average daily gain (ADG) and feed efficiency (FE) in finishing feedlot cattle (conventional beef cattle and Dairy beef). Rumen Culture (RC) is a commercial product manufactured and marketed by Nutrition Physiology Company, LLC (NPC) under the trade name Bovamine®. RC contains about $1 \times 10^7$ of the lactic acid producing bacterium strain LA51 and about $1 \times 10^9$ *Propionibacterium freudenreichii* strain PF24 and is a preferred low-dose DFM for purpose of this disclosure.

Many animal studies on RC are conducted using different diets or cattle types. In order to get an overview of how a treatment performs over a wide range of geographic areas, climates and/or diets, scientists often need to combine (pool) results from different studies. However, when studies are pooled, variations within the studies may not be accounted for. A more recent development in statistical theory, known as Meta-Analysis, which accounts for these variations from individual studies was used on pooled data from the following 19 RC trials.

List of Trials Used in this Study 1. 2008—TTU—Vasconcelos
2. 2008—Oklahoma—Koers-Turgeon
3. 2008—Michigan State—Rust
4. 2007—Idaho—Johnson
5. 2007—Colorado—Wagner
6. 2007—Colorado—Horton
7. 2005—TTU—Galyean
8. 2005—OSU—Krehbiel
9. 2003—TTU—Galyean
10. 2003—Iowa—Trenkle
11. 2003—Idaho—Johnson
12. 2002—TTU—Galyean
13. 2002—NMSU—Elam
14. 2002—NMSU—Elam
15. 2002—Kansas—Garner 16. 2001—Iowa—Trenkle
17. 2000—TTU—Galyean
18. 2000—Michigan—Rust
19. 2000—Colorado—Wagner Treatments and Data A total of 19 feeding trials have been reported comparing the feed performance of controls animals with Bovamine Rumen Culture (RC) supplemented cattle. The RC contained about $1\times10^7$ *Lactobacillus* strain LA51 and about $1\times10^9$ *Propionibacterium freudenreichii* strain PF24. The data included estimated initial body weight as well as the response variables DMI (dry matter intake), ADG (Average Daily Gain), feed to gain ratio (FG) and hot carcass weight (HCW). Standard errors for each response variable by treatment were also provided.

Statistical Analyses

The data were collected by treatment from each trial and pooled. All analyses were performed using the GLIMMIX procedure in SAS (Version 9.2.2). Data were analyzed by scientists at the University of Nebraska-Lincoln using the Meta-Analysis approach (Sauvant et al., 2008 and Glasser et al., 2008). Meta-analytic methods summarize the findings across a number of published studies, where the studies are all testing the same hypotheses. Although the studies were all designed to test the same hypotheses, there were other uncontrollable sources of variability that were uniquely associated with each study, as well as differing numbers of animals included in each study. These factors resulted in heterogeneous variances, which violated the assumption of identical distribution of residual errors (St-Pierre, 2001). St-Pierre (2001) presents an easy remedy by weighting each estimated value, where the weight is the inverse of the standard error squared divided by the mean of the inverse standard errors squared.

Each response variable (DMI, ADG, FG, and HCW) was first analyzed with a model which included fixed effect of treatment (Control or RC), a covariate of initial body weight, a treatment by covariate interaction effect and random study effect. Each response variable was weighted as described. Any non-significant (defined as alpha ≥0.05) interaction term was then dropped and the analysis was re-run. Finally, any non-significant initial body weight covariate was dropped and the analysis was re-run.

Results

There were highly significant differences (p-value<0.01) between the response to Control versus RC for ADG, feed to gain ratio and hot carcass weight. The difference in response for DMI approached statistical significance (p-value<0.10).

According to the output from the Meta-Analysis, RC enhances (P<0.01) ADG by 2.4% and FE by 3.34% (Table 1).

TABLE 1

Summary of the Effects of RC on Feed Performance

| Trait | Least Squares Means (se)[a] | | p-value[b] |
|---|---|---|---|
| | Control | Bovamine | |
| DMI | 20.59 (0.45) | 20.72 (0.45) | 0.0883 |
| ADG | 3.67 (0.08) | 3.76 (0.08) | <0.0001 |
| Feed to Gain Ratio | 5.64 (0.11) | 5.45 (0.11) | <0.0001 |
| Hot Carcass Weight | 812.3 (12.8) | 818.6 (12.8) | 0.0001 |

[a]Least squares means and standard errors are from the model with fixed effect of treatment (and for HCW the covariate of initial body weight) and random effect of study.
[b]the p-values are for the difference between the treatment responses.

In another embodiment, Bovamine® Culture Complex (CC) is utilized to enhance pre-harvest food safety. Culture Complex (CC) is a commercial product manufactured and marketed by Nutrition Physiology Company, LLC (NPC) under the trade name Bovamine®. CC contains about $1\times10^9$ *Lactobacillus acidophilus/animalis* strain LA51 and about $1\times10^9$ *Propionibacterium freudenreichii* strain PF24 and is a preferred high-dose DFM for purpose of this disclosure.

A Meta-analysis conducted by Dr. Loneragan at West Texas A&M University, Canyon, Tex. is described below. Meta-analysis was performed using multiple studies on the effects of Bovamine Culture Complex (CC) over controls on reduction of *E. coli* O157:H7 prevalence in feces and reduction of prevalence on hides.

Figure 2:
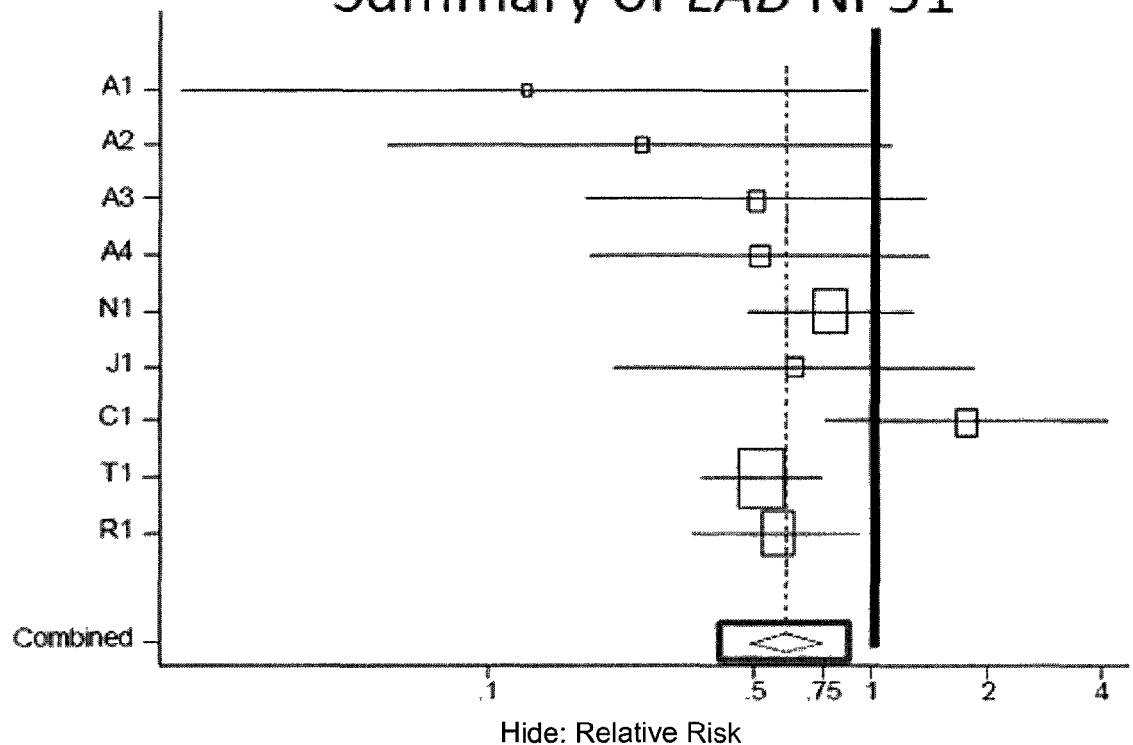
FIG. 2 shows the results of the Meta-analysis showing reduction of O157:H7 prevalence on hides by Bovamine® Culture Complex (CC) over control.
Figure 3:
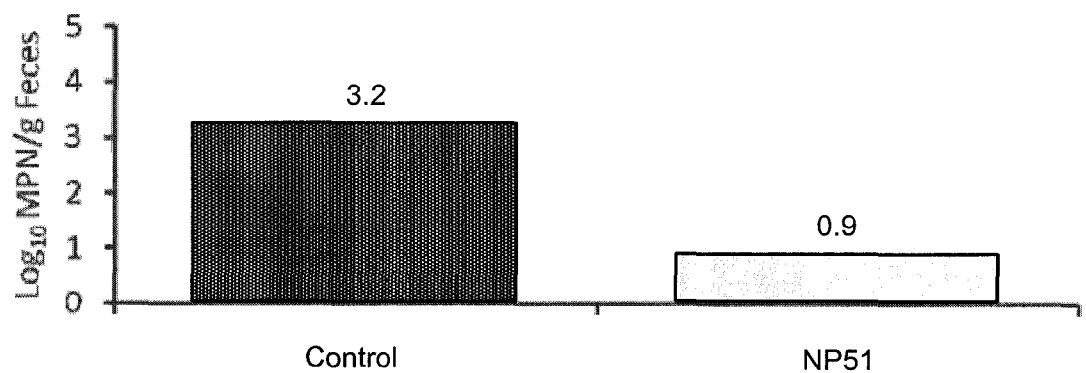
FIG. 3 shows the overall reduction of fecal O157:H7 by LA51 supplement as compared to a control.

FIGS. 1 and 2 show the results of the Meta-analysis showing about 40% reduction of O157:H7 prevalence in feces (26.5 versus 12.7%) by CC over control (FIG. 1) and 47% reduction of O157:H7 prevalence on hides (20.4 versus 11.3%) (FIG. 2). FIG. 3 shows the overall reduction of fecal O157:H7 by CC supplement as compared to a control. CC is associated with reduced numbers of positive animals (animals whose O157:H7 counts are greater than a set threshold value) and reduced numbers of the pathogenic bacteria in the feces of animals that remained positive.

The presently disclosed methods provide a unique combination using low dose and high dose lactic acid producing bacterium to achieve these two seemingly conflicting goals, namely, to enhance feed performance and to reduce pathogens. More specifically, the animals may be fed with feeds that are supplemented with low dosage (about $10^7$ CFU per day per animal) of lactic acid producing bacteria in combination with a relatively high dosage of lactate utilizing bacteria (about $10^9$ CFU per day per animal). At least 14 days, or more preferably, at least 20 days, prior to harvest or sacrifice, the dosage of the lactic acid producing bacteria may be increased to about $10^9$ CFU per day per animal, while maintaining a similar dosage of the lactate utilizing bacteria at about $10^9$ CFU per day. The present methods help reduce the numbers of pathogens in the animals and increase feed performance as measured by average daily gain (ADG) and feed efficiency (F:G) while only modestly increasing the feeding cost.

As used herein, the term "pathogen" refers to a microorganism that may be harmful to a host animal. In a preferred embodiment, "pathogen" refers to those microorganisms that infect meat animals or dairy animals which can subsequently infect the human food supply, thus causing various diseases in humans. The most common pathogenic bacteria include but are not limited to *E. coli*, *Salmonella* spp. such as *Salmonella typhimurium*, and *Staphylococcus aureus*.

Various commercially available products are described or used in this disclosure. It is to be recognized that these products are cited for purpose of illustration only. Certain physical or chemical properties and composition of the products may be modified without departing from the spirit of the present disclosure. One of ordinary skill in the art may appreciate that under certain circumstances, it may be more desirable or more convenient to alter the physical and/or chemical characteristics or composition of one or more of these products in order to achieve the same or similar objectives as taught by this disclosure.

It is to be noted that, as used in this specification and the claims, the singular forms "a," "an," and "the" include plural referents unless the context clearly dictates otherwise. Thus, for example, reference to "a pathogen" includes reference to a mixture of two or more pathogens, reference to "a lactic acid producing bacterium" includes reference to bacterial cells that are lactic acid producing bacteria.

The terms "between" and "at least" as used herein are inclusive. For example, a range of "between 5 and 10" means any amount equal to or greater than 5 but equal to or smaller than 10.

For purpose of this disclosure, the term "precede" means one event or step is started before a second event or step is started.

The dosage of the bacterial supplements is defined by "CFU per day," which refers to the number of colony forming units of the particular bacteria that are administered on the days when the bacteria are administered.

The phrase "continuously on a daily basis" means a step is performed every day during a specified period of time without interruption. Conversely, the term "discontinuous," as used herein, means a step is not performed every day during a specified period of time, or in other words, the step is not performed on at least one day during a specified period of time.

The term "low dose" is used throughout this disclosure, which refers to the supplement of between $1 \times 10^5$ and $5 \times 10^7$ CFU per day of lactic acid producing bacteria, either alone or in conjunction with a fixed dosage of between $5 \times 10^8$ and $5 \times 10^9$ CFU per day of lactate utilizing bacteria. The term "high dose" is also used throughout this disclosure, which refers to the supplement of between $5 \times 10^8$ and $5 \times 10^9$ CFU per day of lactic acid producing bacteria, either alone or in conjunction with a fixed dosage of around $5 \times 10^8$ and $5 \times 10^9$ CFU per day of lactate utilizing bacteria.

Administration of the bacterial supplements may be through oral ingestion with or without feed or water. Preferably, the bacterial supplements are administered along with normal feed or water. The bacteria may be prepared in the form of a lyophilized culture before being mixed with water for spraying or blending with animal feed. The final mixture may be in dry or wet form, and may contain additional carriers that are added to the normal feed of the animal. The normal feed may include one or more ingredients such as corn, cereal grains, corn by-products, cereal grain by-products, alfalfa hay, corn silage, small grain silage, grass hay, plant stalks, oil seed by-products, protein meals, urea, minerals, molasses, and various fat and oil products. The lyophilized cultures may also be suspended in various oils, water and/or compounds for providing a drench to be supplied directly to the animal and the digestive tract of the animal. The lyophilized cultures may also be added to the drinking water of the animals.

Preparation of the DFM or probiotics to be mixed with feed or water may be performed as described in U.S. Pat. No. 7,063,836. Detection and enumeration of pathogenic bacteria may be conducted as described in Stephens et al. (2007). Determination of various feed performance indicators, such as DMI, ADG, FG, and HCW, may be done as described in Vasconcelos et al. (2008). The contents of these references are hereby expressly incorporated by reference into this disclosure.

In one embodiment, the lactic acid producing bacterium may be selected from the group consisting of: *Bacillus subtilis*, *Bifidobacterium adolescentis*, *Bifidobacterium animalis*, *Bifidobacterium bifidum*, *Bifidobacterium infantis*, *Bifidobacterium longum*, *Bifidobacterium thermophilum*, *Lactobacillus acidophilus*, *Lactobacillus agilis*, *Lactobacillus alactosus*, *Lactobacillus alimentarius*, *Lactobacillus amylophilus*, *Lactobacillus amylovorans*, *Lactobacillus amylovorus*, *Lactobacillus animalis*, *Lactobacillus batatas*, *Lactobacillus bavaricus*, *Lactobacillus bifermentans*, *Lactobacillus bifidus*, *Lactobacillus brevis*, *Lactobacillus buchnerii*, *Lactobacillus bulgaricus*, *Lactobacillus catenaforme*, *Lactobacillus casei*, *Lactobacillus cellobiosus*, *Lactobacillus collinoides*, *Lactobacillus confusus*, *Lactobacillus coprophilus*, *Lactobacillus coryniformis*, *Lactobacillus corynoides*, *Lactobacillus crispatus*, *Lactobacillus curvatus*, *Lactobacillus delbrueckii*, *Lactobacillus desidiosus*, *Lactobacillus divergens*, *Lactobacillus enterii*, *Lactobacillus farciminis*, *Lactobacillus fermentum*, *Lactobacillus frigidus*, *Lactobacillus fructivorans*, *Lactobacillus fructosus*, *Lactobacillus gasseri*, *Lactobacillus halotolerans*, *Lactobacillus helveticus*, *Lactobacillus heterohiochii*, *Lactobacillus hilgardii*, *Lactobacillus hordniae*, *Lactobacillus inulinus*, *Lactobacillus jensenii*, *Lactobacillus jugurti*, *Lactobacillus kandleri*, *Lactobacillus kefir*, *Lactobacillus lactis*, *Lactobacillus leichmannii*, *Lactobacillus lindneri*, *Lactobacillus malefermentans*, *Lactobacillus mali*, *Lactobacillus maltaromicus*, *Lactobacillus minor*, *Lactobacillus minutus*, *Lactobacillus mobilis*, *Lactobacillus murinus*, *Lactobacillus pentosus*, *Lactobacillus plantarum*, *Lactobacillus pseudoplantarum*, *Lactobacillus reuteri*, *Lactobacillus rhamnosus*, *Lactobacillus rogosae*, *Lactobacillus tolerans*, *Lactobacillus torquens*, *Lactobacillus ruminis*, *Lactobacillus sake*, *Lactobacillus salivarius*, *Lactobacillus sanfrancisco*, *Lactobacillus sharpeae*, *Lactobacillus trichodes*, *Lactobacillus vaccinostercus*, *Lactobacillus viridescens*, *Lactobacillus vitulinus*, *Lactobacillus xylosus*, *Lactobacillus yamanashiensis*, *Lactobacillus zeae*, *Pediococcus acidilactici*, *Pediococcus pentosaceus*, *Streptococcus cremoris*, *Streptococcus diacetylactis*, *Streptococcus* (*Enterococcus*) *faecium*, *Streptococcus intermedius*, *Streptococcus lactis*, *Streptococcus thermophilus*, and combinations thereof.

The lactate utilizing bacterium may be selected from the group consisting of *Megasphaera elsdenii*, *Peptostreptococcus asaccharolyticus*, *Propionibacterium freudenreichii*, *Propionibacterium acidipropionici*, *Propionibacterium globosum*, *Propionibacterium jensenii*, *Propionibacterium shermanii*, *Propionibacterium* spp., *Selenomonas ruminantium*, and combinations thereof.

For purpose of this disclosure, the preferred lactic acid producing bacterium is *Lactobacillus acidophilus* and *Lactobacillus animalis*, while the preferred lactate utilizing bacterium is *Propionibacterium freudenreichii*. Examples of the lactic acid producing bacterium strains may include but are not limited to the C28, M35, LA45, LA51 and L411. The most preferred lactic acid producing bacterium strain is LA51. The term *Lactobacillus acidophilus/animalis* is used to indicate that either *Lactobacillus acidophilus* or *Lactobacillus animalis* may be used. It is worth noting that when strain LA51 was first isolated, it was identified as a *Lactobacillus acidophilus* by using an identification method based on positive or negative reactions to an array of growth substrates and other compounds (e.g., API 50-CHL or Biolog test). Using modern genetic methods, however, strain LA51 has recently been identified as belonging to the species *Lactobacillus animalis* (unpublished results). Regardless of the possible taxonomic changes for LA51, the strain LA51 remains the same as the one that has been deposited with ATCC.

*Lactobacillus* strains C28, M35, LA45, and LA51 strains were deposited with the American Type Culture Collection (ATCC) on May 25, 2005 and have the Deposit numbers of PTA-6748, PTA-6751, PTA-6749, and PTA-6750, respectively.

Examples of *Propionibacterium freudenreichii* strains may include but are not limited to the P9, PF24, P42, P93 and P99 strains. The most preferred *Propionibacterium freudenreichii* strain is PF24. *Propionibacterium* strain PF24 was deposited with the ATCC on May 25, 2005 and has the Deposit numbers of PTA-6752. P9 and P42 were deposited with the ATCC on Jun. 30, 2005 and have the Deposit numbers of PTA-6821 and PTA-6822, respectively.

EXAMPLES

The following examples are provided to illustrate the present invention, but are not intended to be limiting. The feed ingredients and supplements are presented as typical components, and various substitutions or modifications may be made in view of the foregoing disclosure by one of skills in the art without departing from the principle and spirit of the present invention.

Certain feeding tests described in the Examples contain ingredients that are in a size suitable for a small scale setting. It is important to note that these small scale experiments may be scaled up and the principle of operation and the proportion of each ingredient in the system may equally apply to a larger scale feeding system. Unless otherwise specified, the percentages of ingredients used in this disclosure are on a w/w basis.

Example 1

Low Dose/High Dose Feeding of *Lactobacillus acidophilus/animalis* in Combination with a Fixed Dosage of *Propionibacterium freudenreichii*

Beef cattle are fed with normal feed such as steam-flaked corn-based diet. Sixty days prior to when the cattle are scheduled to be harvested, all animals start to receive a low dose supplemental DFM in addition to their normal feed. The low dose DFM contains *Lactobacillus acidophilus/animalis* strain LA51 and *Propionibacterium freudenreichii* strain PF24 in an amount such that each animal's intake of the *Lactobacillus acidophilus/animalis* strain LA51 is about $1 \times 10^7$ CFU per day and the intake of *Propionibacterium freudenreichii* strain PF24 is about $1 \times 10^9$ CFU per day.

After 30 days on the low dose DFM supplement, the cattle are switched to a feed containing a high dose supplemental DFM in addition to the normal feed. During this high dose period which lasts about 30 days before the animals are slaughtered, the daily intake of *Propionibacterium freudenreichii* strain PF24 remains the same at about $1 \times 10^9$ CFU per day, but the daily intake of *Lactobacillus acidophilus/animalis* strain LA51 is increased to about $1 \times 10^9$ CFU per day.

Example 2

Low Dose/High Dose Feeding of *Lactobacillus acidophilus/animalis* alone to Maximize Feed Performance and Pathogen Reduction Beef cattle are fed with normal feed such as steam-flaked corn-based diet. About one hundred and eighty days prior to when the cattle are scheduled to be harvested, all animals start to receive a low dose supplemental DFM in addition to their normal feed. The low dose DFM contains *Lactobacillus acidophilus/animalis* strain LA51 in an amount such that each animal's intake of the *Lactobacillus acidophilus/animalis* strain LA51 is about $1 \times 10^7$ CFU per day.

After 150 days on the low dose DFM supplement, the cattle are switched to a feed containing a high dose supplemental DFM in addition to the normal feed. During this high dose period which lasts about 30 days before the animals are to be slaughtered, the daily intake of *Lactobacillus acidophilus/animalis* strain LA51 is increased to about $1 \times 10^9$ CFU per day.

LIST OF REFERENCES

The following references and patents and publication of patent applications are either cited in this disclosure or are of relevance to the present disclosure. All documents listed below, along with other papers, patents and publication of patent applications cited throughout this disclosures, are hereby incorporated by reference as if the full contents are reproduced herein:

Glasser F, Ferlay A, Doreau M, Schmidely P, Sauvant D, Chilliard Y., Long-chain fatty acid metabolism in dairy cows: a meta-analysis of milk fatty acid yield in relation to duodenal flows and de novo synthesis. J Dairy Sci. 2008 July; 91(7):2771-85 (2008).

Stephens, et al., *Journal of Food Protection*, Vol. 70, No. 10, Pages 2386-2391 (2007).

Vasconcelos et al., *J. Animal Science*, 86:756-762 (2008).

Patent Documents

| | | |
|---|---|---|
| 5,529,793 | June 1996 | Garner and Ware |
| 5,534,271 | July 1996 | Ware and Garner |
| 7,063,836 | June 2006 | Garner and Ware |
| 7,291,326 | November 2007 | Ware and Brashears |
| 7,291,327 | November 2007 | Garner and Ware |
| 7,291,328 | November 2007 | Garner and Ware |

We claim:

1. A method for reducing the numbers of pathogens and/or for enhancing feed efficiency in cattle, said method comprising:
   (a) administering to said cattle at least one lactic acid producing bacterium for at least 30 days, wherein said lactic acid producing bacterium is administered to said cattle at a dosage of between $1 \times 10^5$ and $5 \times 10^7$ colony forming units (CFU) per day; and
   (b) administering to said cattle at least one lactic acid producing bacterium for at least 20 days, wherein said lactic acid producing bacterium is administered to said cattle at a dosage of between $5 \times 10^8$ and $5 \times 10^9$ CFU per day,
   wherein step (a) precedes step (b), said step (a) being started 120-360 days prior to harvesting said cattle and continued to 20-60 days prior to harvesting, wherein the time period between end of step (a) and start of step (b) is from 0 to 10 days.

2. The method of claim 1, wherein said at least one lactic acid producing bacterium is a strain selected from the group consisting of C28, LA45, LA51 and L411 strains.

3. The method of claim 2, wherein the strain is the LA51 strain.

4. The method of claim 1, wherein step (b) is performed for 20-60 days.

5. The method of claim 1, wherein the administration of said at least one lactic acid producing bacterium in step (a) or (b) is performed continuously on a daily basis.

6. The method of claim 1, wherein said lactic acid producing bacterium is administered in step (a) to said cattle at a dosage of between $8 \times 10^6$ and $2 \times 10^7$ CFU per day.

7. The method of claim 1, wherein said lactic acid producing bacterium is administered in step (b) to said cattle at a dosage of between $8 \times 10^8$ and $2 \times 10^9$ CFU per day.

8. The method of claim 1, wherein both steps (a) and (b) further comprise administering to said cattle at least one lactate utilizing bacterium, wherein said step (a) comprises administering to said cattle at least one lactic acid producing bacterium and at least one lactate utilizing bacterium for at least 30 days, said lactic acid producing bacterium being administered to said cattle at a dosage of between $1\times10^6$ and $5\times10^7$ CFU per day, and said lactate utilizing bacterium being administered to said cattle at a dosage of between $5\times10^8$ and $5\times10^9$ CFU per day; and wherein said step (b) comprises administering to said cattle at least one lactic acid producing bacterium and at least one lactate utilizing bacterium for at least 20 days, said lactic acid producing bacterium being administered to said cattle at a dosage of between $5\times10^8$ and $5\times10^9$ CFU per day, and said lactate utilizing bacterium being administered to said cattle at a dosage of between $5\times10^8$ and $5\times10^9$ CFU per day, wherein step (a) precedes step (b), and said at least one lactic acid producing bacterium is a strain selected from the group consisting of C28, LA45, LA51 and L411 strains, and said at least one lactate utilizing bacterium is a *Propionibacterium freudenreichii* strain selected from the group consisting of P9, PF24, P42, P93 and P99 strains.

9. The method of claim 1, wherein said step (a) further comprises administering to said cattle at least one lactate utilizing bacterium for at least 30 days, wherein said lactate utilizing bacterium is administered to said cattle at a dosage of between $5\times10^8$ and $5\times10^9$ CFU per day; and wherein said step (b) further comprises administering to said cattle at least one lactate utilizing bacterium for at least 20 days, wherein said lactate utilizing bacterium is administered to said cattle at a dosage of between $5\times10^8$ and $5\times10^9$ CFU per day.

10. The method of claim 9, wherein said at least one lactic acid producing bacterium is a *Lactobacillus acidophilus/animalis* strain selected from the group consisting of C28, M35, LA45, LA51 and L411 strains.

11. The method of claim 9, wherein the pathogen is selected from the group consisting of *Escherichia coli*, *Salmonella* spp., and *Staphylococcus aureus*.

12. The method of claim 9, wherein said lactic acid producing bacterium is administered in step (a) to said cattle at a dosage of about $1\times10^7$ CFU per day.

13. The method of claim 9, wherein said lactic acid producing bacterium is administered in step (b) to said cattle at a dosage of about $1\times10^9$ CFU per day.

14. The method of claim 9, wherein said lactate utilizing bacterium is administered in steps (a) and (b) to said animal cattle at a dosage of between $8\times10^8$ and $2\times10^9$ CFU per day.

15. The method of claim 9, wherein said lactate utilizing bacterium is administered in steps (a) and (b) to said cattle at a dosage of about $1\times10^9$ CFU per day.

16. The method of claim 9, wherein the administration in step (a) or step (b) is performed discontinuously.

* * * * *